United States Patent [19]
Raney

[11] Patent Number: 4,577,927
[45] Date of Patent: Mar. 25, 1986

[54] PORTABLE UNITARY BATTERY POWERED HAND-HELD MAGNIFYING APPARATUS

[76] Inventor: Gerard E. Raney, 1278 Edgewood Rd., Redwood City, Calif. 94062

[21] Appl. No.: 472,731

[22] Filed: Mar. 7, 1983

[51] Int. Cl.$^4$ .................. G02B 25/02; G02B 27/04
[52] U.S. Cl. ................................ 350/235; 350/250
[58] Field of Search ............... 350/235, 238, 243-244, 350/250, 257; 356/30-31; 362/455-456; 351/51-59

[56] References Cited

U.S. PATENT DOCUMENTS

| | | | |
|---|---|---|---|
| 2,150,916 | 3/1939 | Forgea | 350/235 |
| 2,178,371 | 10/1939 | Eichenberger | 350/235 |
| 3,837,735 | 9/1974 | Guillet | 351/153 |

FOREIGN PATENT DOCUMENTS

| | | | |
|---|---|---|---|
| 1158873 | 6/1958 | France | 350/235 |
| 191332 | 8/1937 | Switzerland | 362/455 |
| 463778 | 4/1937 | United Kingdom | 350/235 |
| 537151 | 6/1941 | United Kingdom | 350/235 |

OTHER PUBLICATIONS

"The Optical Industry & Systems Directory" 1976, Published by the Optical Publishing Co., pp. D-23.

*Primary Examiner*—William H. Punter
*Attorney, Agent, or Firm*—Flehr, Hohbach, Test, Albritton & Herbert

[57] ABSTRACT

A portable unitary battery powered hand-held magnifying apparatus which is especially useful for examining gems includes a tubular battery casing with a penlight bulb mounted at its end to provide the necessary dark field illumination for showing inclusions in a gem. A ten power triplet type magnifying lens is hingedly mounted to the end of the tube for convenient carrying but when moved 90° its lens' axis is then perpendicular to the nominal light axis. The light bulb is in a parabolic reflector to provide substantially parallel rays. The focal distance of the lens is at the light axis where a gem would be placed for examination.

9 Claims, 2 Drawing Figures

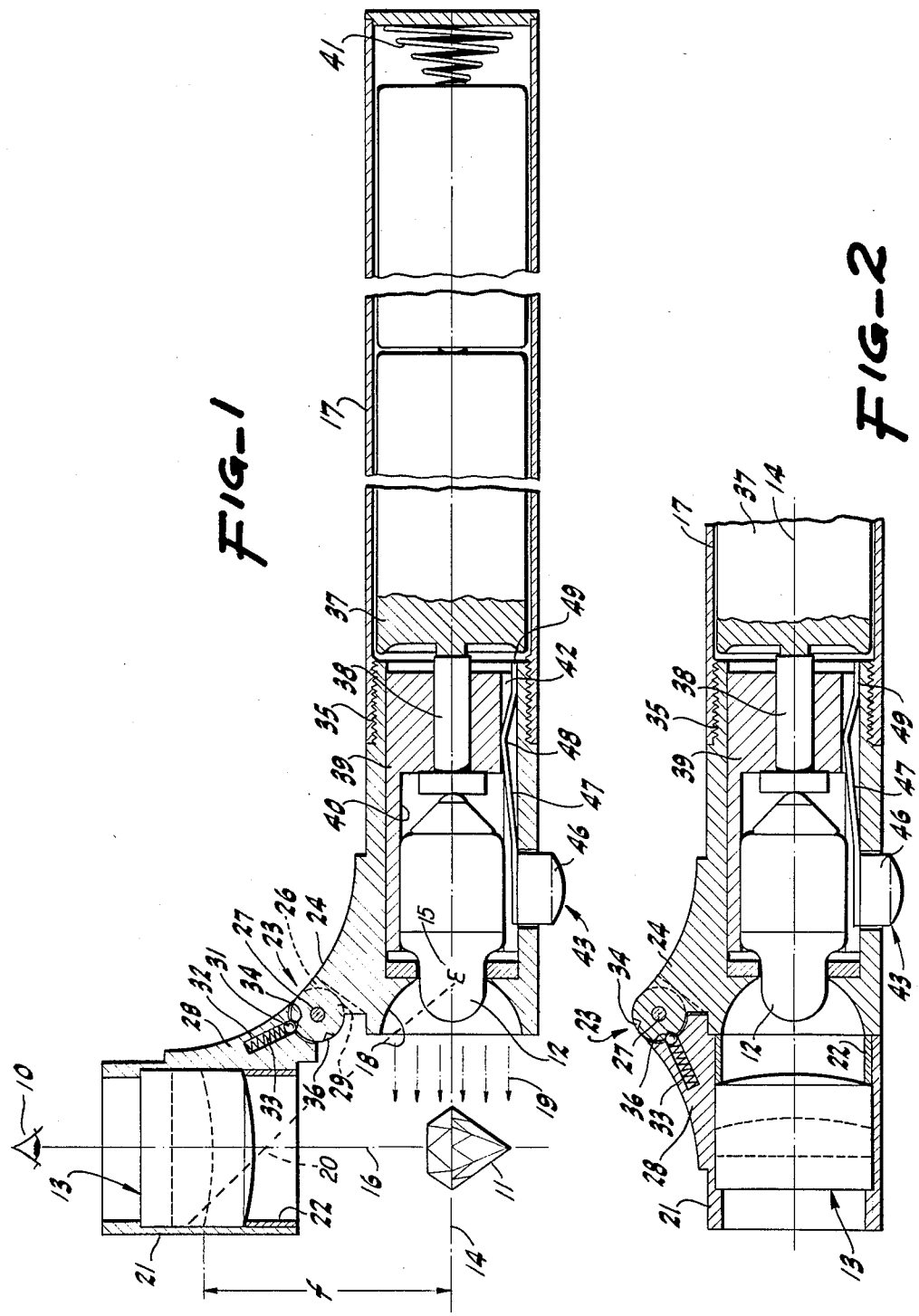

PORTABLE UNITARY BATTERY POWERED HAND-HELD MAGNIFYING APPARATUS

The present invention is directed to a portable unitary battery powered hand-held magnifying apparatus and more specifically to a device for examining gems.

Dark field illumination of gems has long been known as a technique for evaluating the gem and determining defects or inclusions as well as its facets, design and quality in cutting. Classical dark field illumination with a microscope is well known where the specimen is placed at the concentration of a light cone and it is seen by the telescope with the light scattered or diffracted by it.

Portable hand-held units for examining gems are known which are battery powered. For example, one is manufactured by the P. W. Allen Company of London, England which uses a magnifying glass and a light source which provides surface or oblique illumination. This is not sufficient to clearly show inclusions in a gem where dark field illumination is a necessity. Another commercial unit is a portable penlight with a tweezer extending from the end where a gem may be held. While providing dark field illumination, any magnifying unit must be separately held.

A U.S. Pat. No. 2,178,371 to Eichenberger shows a combination flash light and magnifying glass where when reading, for example, gas or electric meters the magnifying lens may be flipped up and the gas meter read. Here, of course, the focal point of the magnifying glass (which is believed to be relatively uncritical) is far below the light since a meter is being read. Thus, it is not suitable for the present purpose because it does not have dark field illumination. Similarly, a French Pat. No. 1,158,873, granted Feb. 3, 1958, shows a "loupe" where again as in the meter reading device the focal length of the lens is at the bottom of a cut-off cylinder. Apparently it is used in medical work for examining ears and eyes as well as surfaces. Thus, this suffers the same defect. In addition, the lens is not collapsible into a simply stored unit.

Thus, it is an object of the present invention to provide an improved portable unitary battery powered hand-held magnifying apparatus.

In accordance with the foregoing, there is provided a portable unitary battery powered hand-held magnifying apparatus which comprises a light source having substantially parallel rays centered around a nominal axis. A viewing lens has an optical axis perpendicular to the light axis and a focal point substantially at the nominal light axis when it is in an operating position. There is a means for holding and retaining the lens. A tubular battery case holds battery means to power the light source and also retains the light source and further includes actuating means for energizing the light source. Hinge means connects the lens holding means to the battery case for allowing the holding means to be folded down on the battery case to form an essentially continuous tubular like structure. The hinge means when opened in its operating position offsets the lens axis from the light source to prevent substantially all direct rays from the light source from entering the lens whereby dark field illumination of a specimen which is placed at the intersection of the focal point of the lens and the optical axis is accomplished to illuminate inclusions in the specimen.

FIG. 1 is a cross-sectional view of apparatus incorporating the invention showing it in an operating position.

FIG. 2 is a cross-sectional view of the apparatus of FIG. 1 with portions eliminated showing it in a stowed position.

FIG. 1 illustrates the invention in its operating position where the eye of a viewer indicated at 10 may observe a specimen or gem 11 (which is held in place by the viewer's hand or other instrument) under the dark field illumination of the light source 12. A ten power triplet type lens 13 provides the proper magnification and has a focal length f, (for example, 25 millimeters) so that its focal point is coincident with or lies on the axis 14 of light source 12. In its operating position, the lens axis 16 is perpendicular to light axis 14. Lens 13 is of the triplet type, for example it may be termed a Hastings triplet lens, and is corrected both for spherical and chromatic aberrations. This is, of course, a necessity when examining a gem since the color purity of the gem must be evaluated as well as its cutting and its facets. Moreover, the dark field illumination provided by light source 12 aptly illuminates any inclusions in the gem 11. Although lens 13 is indicated as a triplet type and as shown by the dashed lines consists of three separate components, in some applications, a single lens or for that matter other types of lens having the appropriate focal length and magnifying power could also be used.

Light source 12 in general is retained by the cylindrical or tubular battery casing 17 which terminates in the parabolic reflector 18 through which the light source 12 (which, for example, may be a G.E. Model No. 222 Penlight bulb) extends so that its filament 15 is essentially in the focus of the parabolic reflector 18. This thus produces substantially parallel light rays 19 to illuminate gem 11. In addition, the parabolic reflector shields the light source from the viewer's eye 10 and the lens 13 to prevent direct light rays from entering the lens and then the eye 10 (see dashed line 20). This, of course, is a necessity in providing for dark field illumination.

Lens 13 is held by a cylindrical sleeve 21 into which lens 13 is inserted and then a retaining ring 22 is pressed in sleeve 21 to fix the lens.

A hinge 23 connects lens holder 21 to battery case 17. Hinge 23 has a fixed portion 24 affixed to tubular casing 17 terminating in a thinner pivot portion 26 having a pin 27 extending therethrough and includes a movable portion 28 connected to the lens holder 21 which has a bifurcated end 29 which is slid over the upstanding end 26 and pinned to it by pin 27.

The hinge is held or detented in the operating position shown in FIG. 1 where a gem is to be observed by a detent formed by a ball 31 located in a channel 32 in the movable hinge portion 28 and spring biased by a spring 33 against a rounded out portion 34 in the fixed portion 26 of the hinge. When the holder 21 is rotated downwardly as illustrated in FIG. 2 so that it abuts against casing 17 to form an essentially continuous tubular like structure, ball 31 is biased against the rounded out portion 36. Thus, FIG. 2 illustrates the stowed position.

Referring again to FIG. 1 as is apparent the hinge 23 offsets in both horizontal and vertical directions the lens 13 in a manner so as to prevent substantially all direct rays from the light source from entering the lens to thus provide for dark field illumination. Reflector 18, of course, also shields the light source and prevents excess dispersion of the light rays 19. In addition, the axis 16 of the lens is displaced from the end of reflector 18 and casing 17 a sufficient distance to leave space for relatively large specimens 11 to be positioned at the focal point of the lens.

Battery case 17 carries two AA penlight batteries, one of which is indicated at 37, to provide energy for the penlight bulb 12. To allow insertion of batteries and light bulbs, the case has a threaded coupling 35. A conductive stud 38 is mounted in a plastic sleeve 39 to connect the end of the battery terminal with bulb 12. A spring 41 at the other end of casing 17 biases the battery against stud 38. Plastic sleeve 39 is slidable in the battery casing and has a cylindrical interior, as illustrated at 40, in which the bulb 12 may be inserted.

As shown also in FIG. 2, actuating means 43 for energizing light source 12 includes a hemispherical button 46 extending through an aperture in the side of battery case 17. A leaf spring 47 has one end permanently attached to button 45 and its other end 49 in contact with casing 17. End 49 is also bent with the apex 48 of the bend being thereby biased against channel 42. This also keeps the other end of spring 47, which is juxtaposed with conductive portion 44 of bulb 12, spaced away from it. However, when pressed or actuated by the user from its resting position, the metal leaf spring makes contact with the conducting bulb portion and thus an electrical connection is made between the bulb and the battery casing to energize the light bulb.

Thus, in summary, when not in use the portable magnifying apparatus is folded together and appears as illustrated in FIG. 2. However, when in the operating position, it provides a very effective and unique technique of dark field illumination of a gem specimen without the need of an expensive microscope but while still providing microscope like quality in evaluating the gem specimen.

What is claimed:

1. A portable unitary battery powered hand-held magnifying apparatus where the eye of a viewer may observe a specimen comprising:
    a light source having substantially parallel rays centered around a light axis;
    a viewing lens having an optical axis perpendicular to said light axis and a focal point substantially at said light axis when in an operating position;
    means for holding and retaining said lens;
    a tubular battery case for holding battery means to power said light source and also for retaining said light source and including actuating means for energizing said light source;
    hinge means for connecting said lens holding means to said battery case for allowing said holding means to be folded down onto said battery case in a stowed position to form an essentially continuous tubular like structure;
    said hinge means, when opened in said operating position, placing said optical axis perpendicular to said light axis, and offsetting said lens from said light source to prevent substantially all direct rays from the light source from entering said lens and the eye of said viewer whereby dark field illumination of said specimen which is placed at the intersection of the focal point of said lens and said light axis is accomplished to illuminate inclusions in said specimen.

2. Apparatus as in claim 1 where said light source is recessed in a parabolic reflector which serves as the termination of said tubular battery case to both shield the light source to prevent direct light rays from entering said lens and the eye of said viewer and also to provide said substantially parallel light rays.

3. An apparatus as in claim 1 where said lens is of the triplet type which has been corrected both for chromatic and spherical aberrations.

4. An apparatus as in claim 2 where said optical axis, in its operating position, is displaced from the end of said light reflector a sufficient distance to leave space for large specimens to be positioned at said focal point.

5. An apparatus as in claim 1 where said stowed position of said optical axis and said light axis coincide.

6. An apparatus as in claim 1 in which said battery case includes a cut-away insulating plastic sleeve slidable in said battery case carrying said light source which is in the form of a penlight bulb.

7. An apparatus as in claim 6 where said plastic sleeve includes a channel along its longitudinal periphery and where said means for actuating said light source includes pushbutton means having a hemispherical button extending through an aperture in the side of said battery case and a leaf spring having one end permanently attached to the spherical pushbutton and the other end permanently bent with the apex of the bend being biased against said channel and the other end of the spring making contact with the battery casing, said leaf spring being juxtaposed and spaced in its resting position from a conductive portion of said light bulb whereby pressing of the hemispherical button by the user allows the metal leaf spring to make contact with the conducting bulb portion and thus an electrical connection between the bulb and the battery casing to be completed to energize said light bulb.

8. An apparatus as in claim 1 where said hinge means includes detent means to detent said lens holding means both in its operating position and in its stowed position.

9. An apparatus as in claim 8 where said detent means includes a spring biased ball located in a channel in the movable portion of said hinge means and rounded out detents in the fixed portion of said hinge means at locations corresponding to said operating and stowed positions.

* * * * *